United States Patent [19]

Kono et al.

[11] Patent Number: 5,292,523

[45] Date of Patent: Mar. 8, 1994

[54] METHOD FOR GROWTH PROMOTION OF ANIMALS AND POWDER COMPOSITIONS CONTAINING KILLED MICROBIAL CELLS OF BACTERIA BELONGING TO GENUS CLOSTRIDIUM

[75] Inventors: Kazumi Kono; Yasuyuki Mizukai, both of Kasukabe; Kazuo Mizuochi, Konosu; Takeshi Asano, Fujioka; Takaichi Murayama, Takasaki; Toshio Kitajo; Mamoru Tanaka, both of Nagano, all of Japan

[73] Assignees: Nippon Kayaku Kabushiki Kaisha, Tokyo; Miyarisan Pharmaceutical Co., Ltd., Toguramachi, both of Japan

[21] Appl. No.: 985,639

[22] Filed: Dec. 3, 1992

[30] Foreign Application Priority Data

Dec. 11, 1991 [JP] Japan .................................. 3-327707
Oct. 23, 1992 [JP] Japan .................................. 4-285834

[51] Int. Cl.$^5$ ......................... A61K 35/74; C12N 1/00; C12N 1/20
[52] U.S. Cl. ............................... 424/520; 424/93 E; 435/842; 426/2
[58] Field of Search ................. 424/93 R, 93 E, 520; 435/252.7, 842, 252.9; 426/2

[56] References Cited

U.S. PATENT DOCUMENTS

| | | | |
|---|---|---|---|
| 2,744,015 | 5/1956 | Katsube et al. | 424/93 E |
| 4,689,226 | 8/1987 | Nurmi et al. | 435/252.9 |
| 4,710,379 | 12/1987 | Kawai et al. | 424/93 |
| 4,808,417 | 2/1989 | Masuda | 426/2 |
| 4,892,731 | 1/1990 | Arai et al. | 424/93 |
| 5,143,845 | 9/1992 | Masuda | 435/252.9 |

FOREIGN PATENT DOCUMENTS

| | | | |
|---|---|---|---|
| 1946661 | 9/1969 | Fed. Rep. of Germany | 424/93 R |
| 2162063 | 1/1986 | United Kingdom . | |
| 2221829 | 2/1990 | United Kingdom . | |
| 2232893 | 1/1991 | United Kingdom . | |

OTHER PUBLICATIONS

Morch, T., "Nordisk Veterinar Medicin." vol. 34, Nov. 1982, pp. 377-387.
Database WPIL Week 9238, Derwent Publications Ltd., London, GB; AN 92-312371.
Database WPIL Week 8817, Derwent Publications Ltd., London, GB; AN 88-116587.
Database WPIL Week 8634, Derwent Publications Ltd., London, GB; AN 86-221293.
Journal of Applied Bacteriology, 66, 365-378 (1989) (referred to as Reference Publication 1.).
Poultry Science, 54, 1643-1646 (1975) (referred to as Reference Publication 2.).
Jpn. J. Med. Mycol. Vo. 28, 262-269, 1987 (referred to as Prior Art reference (1).).
Chikusan-No-Kenkyu, 25(5), 739-740 (1990) (Referred to as Prior Art reference (2).).
Chikusan-No-Kenkyu, 44 (11), 1302-1304 (1990) (Referred to as reference (3).).
Characteristics and Medical Application of Clostridium butyricum Miyairi-p. 1.
ATCC, Quarterly Newsletter, vol. 13, No. 1, 1993. pp. 1-2, 10-11.

*Primary Examiner*—Douglas W. Robinson
*Assistant Examiner*—Kristin Larson
*Attorney, Agent, or Firm*—Nields & Lemack

[57] ABSTRACT

The invention provides a method for the growth promotion of animals, comprising orally administering into animals killed microbial cells of bacteria belonging to the genus Clostridium, and also provides a powder composition, which comprises as essential ingredients killed microbial vegetative cells of bacteria belonging to the genus Clostridium, together with saccharides and-/or starches.

6 Claims, No Drawings

METHOD FOR GROWTH PROMOTION OF ANIMALS AND POWDER COMPOSITIONS CONTAINING KILLED MICROBIAL CELLS OF BACTERIA BELONGING TO GENUS CLOSTRIDIUM

BACKGROUND OF THE INVENTION

1. Field of the Invention

The present invention relates to a method for the growth promotion of animals, and to a powder composition containing killed microbial cells of bacteria belonging to genus Clostridium.

2. Related Art Statement

Antibacterial substances such as antibiotics are widely used as additives for feeds, for the purpose of growth promotion of domestic animals, fowls and cultured aquatic animals.

However, it has been often pointed out by consumers, informants of mass media, etc., that there is a serious problem regarding antibacterial substances found in the flesh of domestic animals, fowls and cultured aquatic animals Therefore, intensive research is being made about the use of antibacterial substances, from a standpoint of the supply of foods safe for human consumption, i.e. highly safe foods.

On the other hand, since old time, use has been made of microbial compositions containing probiotics for the purpose of keeping mammalian animals, including human beings and domestic animals, healthy. It is generally considered that such compositions will have an antagonistic activity against pathogenic bacteria, and that the presence of useful viable bacteria is believed to be indispensable for said compositions accordingly.

In the case of microbial compositions containing probiotics, it is not preferable to heat them in view of protein denaturation, and therefore such compositions cannot be formulated into crumbles and pellets having high strength. In cases where amylase secreting probiotics (such as bacteria belonging to genus Clostridium) are added to the pasty feeds containing α-starch as binders (such as feeds for cultured eels), such feeds may be deteriorated by the action of such amylase. Furthermore, in cases where the probiotics are spore-forming bacteria, it is necessary to subject them to a spore-forming treatment in order to sufficiently avoid the death of bacteria, and therefore such microbial compositions will be produced with a low yield.

It is therefore an object of the invention to provide growth promotion substances, which can be safely used instead of known antibacterial substances and microbial compositions containing probiotics.

SUMMARY OF THE INVENTION

According to the invention, there is provided a method for the growth promotion of animals, which comprises orally administering into the animals killed microbial cells of bacteria belonging to the genus Clostridium. The invention also relates to a powder composition, which comprises, as essential ingredients killed microbial vegetative cells of bacteria belonging to the genus Clostridium, together with saccharides and/or starches.

DETAILED DESCRIPTION OF THE INVENTION

As microorganisms belonging to the genus Clostridium, there may be mentioned, for instance, *Clostridium butyricum*. Especially preferred is *Clostridium butyricum* MIYAIRI, which is commercially available as a probiotics agent from Miyarisan Co., Ltd., Japan. As for said microbial agent, it has been observed that the agent may be administered to human beings and domestic animals for a long period of time without any undesired secondary effects.

As an example of the MIYAIRI species, there may be mentioned *Clostridium butyricum* strain MIYAIRI 588, which has been deposited in the Fermentation Research Institute of the Agency of Industrial Science & Technology of Japan of 1-3, Higashi 1-chrome, Tsukuba-shi, Ibaraki-ken, 305, Japan, on May 1, 1981 as an international deposition under the Budapest Treaty and given Accession No. FERM BP-2789.

As viable microbial cells to be employed in the production of killed cells, use may be made of viable cells of spore-forming stages and vegetative stages without any limitation. Preferred are viable cells of vegetative stages A method for the cultivation of such viable bacteria is described in U.S. Pat. No. 4,892,731.

The killed microbial cells to be employed according to the invention may be obtained in a conventional manner, for instance, by subjecting the corresponding viable microbial cells to a heat treatment or a treatment with formalin or other bactericidal agents. The killed microbial cells may be microbial cells which have been substantially killed. It is also possible to use viable microbial cells if they are substantially killed when they are formulated into a preparation.

The microbial vegetative cells of bacteria belonging to the genus Clostridium may be obtained, for instance, by one of many suitable methods. There are no limitations on methods for the cultivation and the separation of microbial cells. For instance, there is a method, wherein the Clostridium bacteria are inoculated in a suitable culture medium such as a conventional glucose-containing broth and cultured at a temperature of from 30° to 40° C. for a period of from 14 to 24 hours. After the completion of the above-mentioned preliminary cultivation, a main cultivation is carried out, wherein the liquid culture product obtained in the preliminary cultivation is inoculated in a similar culture medium having a bigger size and cultured under temperature and time conditions similar to those employed in the preliminary cultivation. After the completion of the main cultivation, the resulting microbial cells may be harvested by suitable means such as a centrifugal separator. Any culture media for said bacteria may be employed without specific limitations. For instance, use may be made of a conventional broth for *Clostridium butyricum*, comprising 0.8% meat extract, 1% peptone and 0.5% sodium chloride. Generally preferred are liquid culture media containing glucose, yeast extract and peptone.

It is also possible to carry out a method disclosed in Japanese Patent KOKOKU No. 8300/1962, wherein a cultivation operation is effected for a relatively short period of from about 14 to 24 hours, then this operation is interrupted to obtain microbial cells of vegetative stage before the spore-forming stage, and the microbial cells are harvested.

The killed microbial vegetative cells of Clostridium bacteria to be used according to the invention may be obtained by filtering the cultured microbial vegetative cells in air. If the filtration in air is insufficient, then it is possible to suspend the filtered product in water wherein air is present. The bacteria belonging to the genus Clostridium are obligatory anaerobes, and the microbial vegetative cells of bacteria will be killed when they are exposed to air, so that the killed microbial vegetative cells of bacteria will be obtained.

It is also possible to obtain the killed microbial vegetative cells by subjecting the corresponding viable vegetative cells to a heat treatment or a treatment with formalin or other bactericidal agents. The killed microbial cells may be one which has been substantially killed. In addition, use may be made of the viable microbial cells, if they may be substantially killed when they are formulated into preparations.

The dry powder of killed microbial cells used according to the invention described below may be one which contains at least $10^9$, preferably $10^9$–$10^{11}$ as the number of the microbial cells per g of the dry powder. The number of the microbial cells mentioned above is one which has been counted by a method wherein a counting operation is carried out for a suspension of emulsified microbial cells in a physiological salt solution with the aid of a hemacytometer under microscope.

The microbial compositions according to the invention described below may contain at least $10^6$, preferably $10^6$–$10^{11}$, more preferably $10^6$–$10^{10}$ of killed microbial cells per g of the composition.

The animals to be administered with the compositions according to the invention are those other than human beings, including, for instance, domestic animals, fowls, cultured aquatic animals and the like.

The microbial compositions according to the invention may be prepared, for instance, by the following method. After obtaining a liquid culture product by the cultivation of microbial cells, the microbial cells are subjected to a bactericidal treatment and the resulting killed microbial cells are separated and concentrated to give a dry powder. The dry powder of the killed microbial cells thus obtained may be directly formulated into a preparation. It is also possible to mix the dry powder with an excipient allowed according to the Law concerning Safety Assurance and Quality Improvement of Feed of JAPAN, such as defatted rice bran, wheat flour, glucose, silica, wheat bran or the like, to form a preparation. Furthermore, it is possible to concentrate and dry the liquid culture product together with the residue thereof to obtain a sterilized mixture containing the killed microbial cells which may then be used as effective ingredients in a composition according to the invention. The compositions according to the invention may have a form of powder, tablets, pellets, fine granules, capsules, etc.

Such tablets may be prepared in a conventional manner with the optional use of excipients, disintegrating agents, binders, lubricants and the like.

As excipients, there may be mentioned, for instance, saccharides such as lactose, D-mannitol, D-soribitol and sucrose; starches such as corn starch and potato starch; and inorganic salts such as calcium phosphate, calcium sulfate and precipitated calcium carbonate.

Examples of disintegrating agents are starches such as hydroxypropyl starch, sodium carboxymethyl starch and starch which has been partially converted to α-form; cellulose derivatives such as calcium carboxymethyl cellulose, carboxymethyl cellulose and hydroxypropyl cellulose with low substitution degree; and synthetic high polymers such as crosslinked polyvinyl pyrrolidone As binders, it is possible to use, for example, high molecular weight substances including polyvinylpyrrolidone, hydroxypropyl cellulose, hydroxypropylmethyl cellulose, gelatin, gum arabic and the like.

Examples of lubricants are naturally occurring substances and their derivatives such as talc, wax and colloidal silicon dioxide; and fatty acids and metal salts thereof such as stearic acid, magnesium stearate, calcium stearate, aluminium stearate and sucrose fatty acid esters.

In tablets, polymers such as MACROGOL are properly used.

When the compositions according to the invention are employed for the growth promotion of animals, they are generally used as additives for feeds or drinking water. Therefore, in this case, use is preferably made of the compositions having a powder form. Such powder compositions may contain 0.00005–80%, preferably 0.0005–70%, more preferably 0.01–50% of a powder comprising killed microbial cells of bacteria belonging to the genus Clostridium, the balance being carriers.

As for the compositions according to the invention, it may be said that the compositions are preferably ones which contain not only the killed microbial vegetative cells but also saccharides and/or starches, because the growth promotion activity of such preferred compositions is considerably high. Thus, preferred are the powder compositions comprising killed microbial vegetative cells of bacteria belonging to the genus Clostridium, together with saccharides and/or starches.

As saccharides used in the powder compositions containing the killed microbial cells, it is possible to employ any of the saccharides, including, for instance, glucose, fructose, sucrose, oligosaccharides, lactose and the like, although lactose is preferred.

As starches, use may be made of any of the starches such as wheat starch, potato starch and corn starch. Corn starch is preferred.

The dry powder of killed microbial vegetative cells of bacteria belonging to the genus Clostridium should contain at least $10^9$, preferably $10^9$–$10^{11}$ of microbial cells per g of the dry powder.

The powder compositions containing killed microbial vegetative cells of bacteria belonging to the genus Clostridium according to the invention may be prepared, for instance, by a method wherein a powder of killed microbial cells is admixed with powdered saccharides or starches so as to form a homogeneous mixture. Another method comprises admixing a wet substance based on killed microbial cells with saccharides or starches to form a mixture, which is then dried and pulverized. In view of the simplicity of operations, it is preferred to admix killed microbial cells with saccharides and/or starches to form a mixture, which is then suspended in water. The resulting suspension is subjected to a spray drying operation wherein the inlet temperature for hot air is between 120° and 200° C., preferably between 130° and 170° C. and the outlet temperature is between 30° and 150° C., preferably between 50° and 100° C. As for the amount of saccharides and starches added, it may generally be said that the amount of saccharides is between 0.04 and 700 parts by weight of saccharides, preferably between 0.1 and 70 parts by weight, whereas the amount of starch is between 0.2 and 700 parts by weight, preferably between 0.4 and 70 parts by weight per part by weight of the dry powder of the killed microbial vegetative cells of Clostridium bacteria. In the case of the spray drying operations, it is observed that the operations may be effected more easily if use is made, as additives, of physiologically allowed inorganic substances which are sparingly soluble in water, such as calcium carbonate and the like. The amount of such inorganic substances added is between 0.005 and 0.5 part, preferably between 0.01 and 0.2 part, more preferably between 0.01 and 0.1 part on the basis of the total amount of the above-mentioned essential ingredients, the bacteria, starches, and saccharides.

The powder compositions containing the killed microbial vegetative cells of Clostridium bacteria obtained by the method mentioned above generally comprise 0.05-80%, preferably 0.5-70%, more preferably 5-50% of a powder based on killed microbial vegetative cells of Clostridium bacteria, 1-50%, preferably 3-40%, more preferably 5-30% of saccharides, and 15-90%, preferably 25-80%, more preferably 35-75% of starches. The powder compositions may contain at least $10^9$, preferably $10^9$–$10^{11}$, more preferably $10^9$–$10^{10}$ of the killed microbial cells. In cases where the compositions further contain inorganic substances, the amount of inorganic substances is generally between 0.5 and 50%, preferably between 1 and 20%, more preferably between 1 and 10%.

It is also possible to add excipients to the powder compositions. As excipients used, there may be mentioned, for example, any of the excipients allowed according to Law concerning Safety Assurance and Quality Improvement of Feed of Japan, including defatted rice bran, soy bean meal powder, bran chips, rice hull powder, calcium carbonate, saccharides, starches, beer yeast and wheat flour. It is possible to use either one excipient or at least two excipients. The amount of excipients added is generally between 0.01 and 1000 parts by weight, preferably between 0.1 and 800 parts by weight, more preferably between 1-500 parts by weight per part by weight of the powder compositions mentioned above. In the case of the excipient-containing powder compositions, the number of killed microbial cells contained therein is generally at least about $10^6$, preferably between $10^6$ and $10^{11}$, more preferably between $10^6$ and $10^{10}$ per g of the compositions.

The excipient-containing powder compositions essentially comprise 0.00005-80%, preferably 0.0005-70%, more preferably 0.01-25% of a powder based on killed microbial vegetative cells of Clostridium bacteria, 0.001-50%, preferably 0.003-40%, more preferably 0.01-15% of saccharides, 0.015-90%, preferably 0.03-80%, more preferably 0.05-40% starches, and 1-99.9%, preferably 10-99.8%, more preferably 50-99.7% of excipients. If the above-mentioned powder compositions are those prepared by a spray drying operation and further containing inorganic substances, it is suitable that the amount of such inorganic substances is between 0.0005 and 33%, preferably between 0.001 and 15%, more preferably between 0.002 and 5%.

When use is made of saccharides, starches or inorganic substances as excipients, the amount of excipients in the compositions is as follows 0.001-99.9%, preferably 0.003-99.8%, more preferably 0.01-99.7% of saccharides, 0.015-99.9%, preferably 0.03-99.8%, more preferably 0.05-99.7% of starches, and 0.0005-99.9%, preferably 0.001-99.8%, more preferably 0.002-99.7% of inorganic substances.

The compositions according to the invention may be added with additives such as flowability improvers, anti-coagulation agents, anti-scattering agents and the like.

The compositions according to the invention may be administered as such into animals, although the compositions are usually added to feeds or drinking water for domestic animals, fowls or cultured aquatic animals. If necessary, it is possible to effect continuous administrations, usually for a period of from 1 month to several years.

Examples of animals to be administered are domestic animals such as cow, pig, horse and sheep; fowls such as broiler, hen, quail, duck, domestic duck, pheasant and turkey; and cultured aquatic animals such as yellow tail, sea-bream, swellfish, tunny, turbot, horse-mackeral, salmon, carp, eel, rainbow trout, fresh-water trout, shellfish e.g. prawn, crawfish, panulirus, lobster, and black tiger, and crabs e.g. *Paralithodes, Chionoecetes* and *Erimacrus*.

When the compositions are added to feeds, the amount of the compositions added is such that the number of microbial cells is at least about $10^4$, preferably between about $10^4$ and $10^7$, more preferably between about $10^4$ and $10^6$ per g of feeds. For instance, when use is made of compositions containing no excipients, the amount of compositions added may be at least 0.1 ppm, preferably between 0.1 and 1000 ppm, more preferably between 0.1 and 100 ppm. When the compositions containing excipients are used, the amount of compositions may be at least 0.001% by weight, preferably between 0.01 and 10% by weight, more preferably between 0.1 and 0.5% by weight.

When the compositions are added to drinking water, the amount of compositions added is such that the number of microbial cells is at least about $10^4$, preferably between about $10^4$ and $10^7$, more preferably between about $10^4$ and $10^6$ per ml of drinking water. When compositions without excipients are used, the amount of compositions added is generally at least 0.05 ppm, preferably between 0.05 and 500 ppm, more preferably between 0.05 and 50 ppm. In case where the excipient-containing compositions are employed, the amount of compositions added is generally at least 0.0005%, preferably between 0.005 and 5%, more preferably between 0.05 and 0.5%.

The invention and the effects thereof will be further illustrated by the following test results Test 1—1Growth Test of Rainbow Trouts Purpose: In order to observe the growth promotion effect, a number of tests were conducted, wherein dead microbial cells of *Clostridium butyricum* MIYAIRI were added to feeds for rainbow trouts Manner of Tests Sample: Use was made of a feed added with $10^5$ of killed microbial cells of *C. butyricum* MIYAIRI per g of feed.

Procedure: Rainbow trouts, having an average body weight of 20 g per one rainbow trout, were raised for 40 days, with the proviso that the number of rainbow trouts per one section was 525.

The test results are shown in Table 1.

TABLE 1

| | Growth test of rainbow trouts | |
|---|---|---|
| Section | Body weight gain per day (g/fish/day) | Feed efficiency |
| Use of killed microbial cells | 0.23 (110) | 0.73 (106) |
| Use of viable microbial cells | 0.21 (100) | 0.69 (100) |
| Control | 0.21 (100) | 0.69 (100) |

Remark: The parenthesized numbers are index numbers based on 100 corresponding to the value obtained in the control section.

As shown in Table 1, it was observed that the killed microbial cells of C. butyricum MIYAIRI exhibited a growth promotion effect on rainbow trouts.

Test 1-2 Mouse Growth Test

Purpose: In order to observe a growth promotion effect of killed microbial cells of C. butyricum MIYAIRI, the following tests were conducted, wherein the killed microbial cells were added to feeds for mice.

Sample: Use was made of feeds added with $10^5$ or $10^7$ of killed microbial cells of C. butyricum MIYAIRI per g of feeds.

Test procedure: SPF mice, with an average body weight of 25 g per mouse, were raised for a period of 28 days, with the proviso that the number of mice per section was 10.

The test results are shown in Table 2.

TABLE 2

| | Growth test of mice |
|---|---|
| Section | Body weight gain |
| Use of $10^5$ of killed microbial cells/g | 3.80 g (129) |
| Use of $10^7$ of killed microbial cells/g | 4.50 (153) |
| Control | 2.95 (100) |

Remark: The parenthesized numbers are index numbers based on 100 corresponding to the values obtained in the control section.

As shown in Table 2, it was observed that the killed microbial cells of C. butyricum MIYAIRI had a growth promotion effect on the mice.

Test 1-3 Growth test of broilers

Purpose: In order to observe a growth promotion effect of killed microbial cells of C. butyricum MIYAIRI, the following tests were conducted, wherein the killed microbial cells were added to feeds for broilers.

Sample: Use was made of feeds added with $10^6$ of killed microbial cells of C. butyricum MIYAIRI per g of feeds.

Test procedure: Broilers, with an average body weight of 40 g per broiler, were raised for a period of 28 days, with the proviso that the number of broilers per section was 20.

The test results are shown in Table 3.

TABLE 3

| | Growth test of broilers | |
|---|---|---|
| | Body weight gain | Feed conversion |
| Section, wherein killed microbial cells were used | 882 g (104) | 1.57 (98) |
| Control section | 846 g (100) | 1.61 (100) |

Remark: the parenthesized numbers are index numbers based on 100 corresponding to the values obtained in the control section.

As shown in Table 3, it was observed that the killed microbial cells of C. butyricum MIYAIRI had a growth promotion effect on the broilers.

Test 1-4 Test on Deterioration of Feeds for Cultured Eels (i.e., Test on Undesired Scattering of Feeds into Water)

Purpose: The following tests were conducted in order to observe as to whether or not a deterioration occurred on feeds for cultured eels, which had been added with a powder based on viable or killed microbial cells of C. butyricum MIYAIRI.

Test procedure: 100 g of feeds, feed compositions shown in Table 4, were placed in a beaker, and admixed and kneaded with 120 g of water to prepare a rise-cake-like mixture, which was then allowed to stand at 30° C. for 10 minutes, and then formulated into dumpling-like samples having a weight of 10 g per one sample. Each dumpling-like sample contained about $10^5$ of the microbial cells of C. butyricum MIYAIRI per g of sample.

TABLE 4

| | Composition of samples | | |
|---|---|---|---|
| | Control section | Section using viable bacteria | Section using killed bacteria |
| Fish meal | 80% | 80% | 80% |
| Starch converted to α-form | 20% | 19 | 19 |
| Viable bacteria | — | 1 | — |
| Killed bacteria | — | — | 1 |

Each sample was placed in a conical flask with a volume of 300 ml, admixed with 100 ml of water, and shaken for 30 minutes by means of a vibrator provided with a heating device. After the vibration, the sample was allowed to stand for 5 minutes, and then a supernatant liquid thereof was separated. A measurement was made about the transmittance of the supernatant liquid at a wave length of 660 mµ by means of a spectrophotometer. The measurements of each sample were 5 times made, and an average measured value was recorded.

The test results are shown in Table 5.

TABLE 5

| | Test of deterioration of feeds for eels (test on scattering into water) | | |
|---|---|---|---|
| | Control section | Section using viable bacteria | Section using killed bacteria |
| Transmittance | 56.5 (100) | 31.8 (56) | 57.6 (102) |

Remark: The parenthesized numbers are index numbers based on 100 corresponding to the values obtained in the control section.

It was observed from Table 5 that the undesired scattering of the viable microbial cell-added feeds into water was suppressed when use was made of the killed microbial cells instead of viable microbial cells.

Test 2-1 Growth Test of Broilers (1) Samples

Sample according to the invention: Killed microbial composition shown in Example 2-3 (Number of microbial cells: $8.7 \times 10^{10}$/g).

Reference sample: Powder of killed microbial vegetative cells alone shown in Reference Example (Number of microbial cells: $5 \times 10^{11}$/g).

(2) Test Procedure

Broilers of Arbor Acres strain with a body weight of about 44 g, were raised with the provisos that the number of broilers was 20 (i.e. 10 male birds and 10 female birds) per section, and that one test was effected in triplicate. The broilers were raised with a feed for broilers, which was free from any of antibiotics and antibacterial substances and to which had been added with the above-mentioned samples in an amount corresponding to (4.4 to 4.5)$\times 10^5$ of microbial cells per g. The growth test was conducted for a period of 4 weeks. Furthermore, there was a control section, wherein broilers were raised with a feed which was free from the above-mentioned samples.

(3) The test results are shown in Table 6 given below.

TABLE 6

| Section | Growth test of broilers | |
|---|---|---|
| | Body weight gain | Feed conversion |
| Control | 845 g (100) | 1.85 (100) |
| Use of reference sample | 864 g (102) | 1.85 (100) |
| Use of sample according to the invention | 884 g (105) | 1.81 (98) |

As shown in Tests 1—1 to 1-4, the killed microbial cells of C. butyricum MIYAIRI exhibit a growth promotion effect on domestic animals, fowls and cultured aquatic animals, and are hence useful for the production of highly safe meats and cultured aquatic animals. Unlike viable microbial cells, there are no limitations on the preparation of feeds. Particularly, it should be noted that the effects of the invention are remarkable over the use of viable microbial cells, in that the addition of killed microbial bodies to feeds for cultured aquatic animals does not accelerate any deterioration of feeds.

Furthermore, it can be said from the results of Test 2-1 that the powder compositions according to the invention, comprising killed microbial vegetative cells of C. butyricum MIYAIRI together with saccharides and/or starches, have a growth promotion effect higher than that of the related powder compositions comprising killed microbial cells of said bacterium alone. Thus, the compositions according to the invention are effective for an enhancement in the productivity of domestic animals, fowls and aquatic animals.

The invention will be further illustrated in detail by the Examples given below.

EXAMPLE 1—1

| Preparation of powder composition | |
|---|---|
| Defatted rice bran | 96 g |
| Soy bean oil | 3 g |
| Powder of killed microbial cells of C. butyricum MIYAIRI ($10^{10}$ of killed microbial cells per g) | 1 g |

The above-mentioned components were mixed with one another to prepare a powder composition.

EXAMPLE 1-2

| Preparation of Pellet | |
|---|---|
| Defatted rice bran | 70 g |
| Wheat flour | 28.9 g |
| Powder comprising killed microbial cells of C. butyricum MIYAIRI ($10^{10}$ of killed microbial cells per g) | 1 g |
| Sodium polyacrylate | 0.1 g |

These components were mixed with one another, and the resultant mixture was formed into pellets by means of a pellet-forming machine.

EXAMPLE 1-3 Preparation of Tablet 1 part of powder, containing microbial cells of C. butyricum MIYAIRI ($10^{10}$ of killed microbial cells/g) was intimately mixed with 80 parts of lactose, 20 parts of corn starch, 20 parts of hydroxypropyl cellulose, wherein the substitution degree was low, and 2 parts of polyvinylpyrrolidone, and formed into granules, which were then admixed with 0.5 part of magnesium stearate. Then a tablet-forming operation was carried out.

EXAMPLE 1-4 Preparation of Fine Granule 1 part of powder, containing killed microbial cells of C. butyricum MIYAIRI ($10^{10}$ killed microbial cells per g) was intimately mixed with 85 parts of mannitol, 15 parts of carboxymethyl cellulose and 2.5 parts of hydroxypropyl cellulose, and then formed into fine granules.

EXAMPLE 2-1

A stored bacterium, Clostridium butyricum MIYAIRI strain 588 (FERM BP-2789), was cultured on the below-mentioned culture medium at 37° C. After 16 hours, the liquid culture was subjected to a centrifugal separation operation to obtain microbial vegetative cells.

| Peptone | 1% |
|---|---|
| Yeast extract | 1% |
| Glucose | 1% |

100 g of microbial cells thus obtained, 110 g of corn starch, 50 g of lactose and 8 g of calcium carbonate were suspended in 1 liter of water. The resultant suspension was subjected to an instantaneous spray drying operation by means of a spray drier, wherein the inlet temperature for hot air was between 140° and 160° C. and the outlet temperature was between 70° and 95° C., so that a powder composition according to the invention which contained killed microbial vegetative cells was obtained.

EXAMPLE 2—2

300 g of powder containing killed microbial vegetative cells of C. butyricum MIYAIRI were mixed with 100 g of lactose and 600 g of corn starch in a V-type mixer to obtain a powder composition according to the invention.

EXAMPLE 2-3

5.15 kg of powder containing killed microbial vegetative cells of *C. butyricum* MIYAIRI which was obtained by the method like Reference Example described below were emulsified, together with 2 kg of lactose, 13 kg of corn starch and 1 kg of calcium carbonate, in an amount of water. The resulting emulsion was admixed with a further amount of water so as to increase the volume of emulsion to 100 liters. Then a spray drying operation was carried out by means of a spray drier to obtain a powder composition according to the invention.

EXAMPLE 2-4

2 5 kg of powder containing killed microbial vegetative cells of *C. butyricum* MIYAIRI were mixed with 0.5 kg of lactose, 7 kg of corn starch and 90 kg of beer yeast in a drum-type mixer to obtain a powder composition according to the invention.

EXAMPLE 2-5

5 g of the spray dried product shown in Example 2-1 were intimately mixed with 85 g of beer yeast and 10 g of defatted rice-bran to obtain a composition according to the invention.

REFERENCE EXAMPLE

A stored bacterium, *Clostridium butyricum* MIRAIRI strain 588 (FERM BP-2789), was cultured on the below-mentioned culture medium at 37° C. After 16 hours, the liquid culture was subjected to a centrifugal separation operation to obtain microbial vegetative cells.

| Peptone | 1% |
| Yeast extract | 1% |
| Glucose | 1% |

100 g of microbial cells thus obtained were suspended in 350 ml of water. This suspension was subjected to a preliminary freezing operation at $-30°$ C., and then to a conventional freeze-drying operation to obtain a dried powder containing killed microbial vegetative cells.

We claim:

1. A method of promoting growth in an animal which comprises orally administering to the animal killed microbial cells of bacteria belonging to *Clostridium butyricum* in an amount effective to promote growth of the animal.

2. A method according to claim 1, wherein the bacterium belonging to *Clostridium butyricum* is *Clostridium butyricum* MIYAIRI.

3. A method according to claim 1, wherein the killed microbial cells are killed microbial vegetative cells.

4. A method according to claim 1, wherein the killed microbial cells are administered to the animal by adding the killed microbial cells to animal feed.

5. A method according to claim 5, wherein the number of the killed microbial cells in the feed is at least $10^4$ per g of feed.

6. A method according to claim 1, wherein the animal is a domestic animal, a fowl or an aquatic animal.

* * * * *